United States Patent

Galili et al.

[11] Patent Number: 5,811,680
[45] Date of Patent: Sep. 22, 1998

[54] METHOD AND APPARATUS FOR TESTING THE QUALITY OF FRUIT

[75] Inventors: Naftali Galili, Moshav Tel Adashim; Itzhak Shmulevich, Haifa; David Rosenfeld, Ma'alot, all of Israel

[73] Assignee: Technion Research & Development Foundation Ltd., Haifa, Israel

[21] Appl. No.: 557,130

[22] PCT Filed: Jun. 13, 1994

[86] PCT No.: PCT/US94/06869

§ 371 Date: Mar. 20, 1996

§ 102(e) Date: Mar. 20, 1996

[87] PCT Pub. No.: WO94/29715

PCT Pub. Date: Dec. 22, 1994

[30] Foreign Application Priority Data

Jun. 13, 1993 [IL] Israel ........................................ 106005

[51] Int. Cl.[6] .................................................. G01N 29/12
[52] U.S. Cl. ............................ 73/579; 73/584; 73/12.01
[58] Field of Search .................................. 73/579, 12.01, 73/12.04, 12.09, 584, 595, 862.68; 209/556, 590, 599, 558

[56] References Cited

U.S. PATENT DOCUMENTS

| | | | |
|---|---|---|---|
| 2,277,037 | 1/1942 | Clark et al. ................................ | 73/51 |
| 3,465,177 | 9/1969 | Winslow . | |
| 3,470,737 | 10/1969 | Fridley ........................................ | 73/81 |
| 3,648,081 | 3/1972 | Lean et al. ................................ | 310/8.1 |
| 3,680,694 | 8/1972 | Hamann ..................................... | 209/119 |
| 3,969,927 | 7/1976 | Yoshida et al. ............................ | 73/587 |
| 4,061,020 | 12/1977 | Fridley ........................................ | 73/81 |
| 4,216,403 | 8/1980 | Krempl ..................................... | 310/328 |
| 4,316,115 | 2/1982 | Wilson ..................................... | 310/337 |
| 4,413,202 | 11/1983 | Krempl ..................................... | 310/338 |
| 4,491,760 | 1/1985 | Linvill ..................................... | 310/334 |
| 4,535,205 | 8/1985 | Rauinet ............................... | 179/110 A |
| 4,555,953 | 12/1985 | Paolo et al. . | |
| 4,558,249 | 12/1985 | Lerch et al. ............................. | 310/322 |
| 4,712,037 | 12/1987 | Verbeek et al. ........................ | 310/323 |
| 4,761,005 | 8/1988 | French et al. ........................... | 373/1 G |
| 4,869,101 | 9/1989 | Dvorsky .................................... | 73/159 |
| 4,883,271 | 11/1989 | French ................................. | 273/1 GC |
| 4,884,696 | 12/1989 | Peleg ........................................ | 209/545 |
| 4,937,555 | 6/1990 | Litzkow et al. .......................... | 73/587 |
| 5,062,296 | 11/1991 | Migliori .................................... | 73/579 |
| 5,099,702 | 3/1992 | French ................................. | 73/862.68 |
| 5,152,401 | 10/1992 | Affeldt, Jr. et al. .................... | 209/556 |
| 5,396,799 | 3/1995 | Ross et al. ................................ | 73/579 |
| 5,426,977 | 6/1995 | Johnston et al. ......................... | 73/579 |

FOREIGN PATENT DOCUMENTS

| | | |
|---|---|---|
| 267737 | 6/1988 | European Pat. Off. . |
| 295907 | 12/1988 | European Pat. Off. . |
| 439405 | 7/1991 | European Pat. Off. . |
| 450716 | 10/1991 | European Pat. Off. . |
| 526364 | 2/1993 | European Pat. Off. . |
| 275025 | 3/1987 | Germany . |
| 1-274059 | 11/1989 | Japan . |
| 5-118933 | 5/1993 | Japan . |
| 523352 | 8/1976 | U.S.S.R. . |
| 570358 | 10/1977 | U.S.S.R. . |
| 615415 | 6/1978 | U.S.S.R. . |
| 835337 | 6/1981 | U.S.S.R. . |
| 2160388 | 12/1985 | United Kingdom . |

*Primary Examiner*—Hezron E. Williams
*Assistant Examiner*—Nashmiya Fayyaz
*Attorney, Agent, or Firm*—Ladas & Parry

[57] ABSTRACT

A method of testing the quality of a fruit including applying a dynamic impact force to the fruit, detecting the mechanical response of the fruit to the dynamic force via a piezoelectric film transducer supported on a displaceable resilient base member such that the film transducer is bent by the dynamic impact force, to induce a strain in the film transducer, and the film transducer outputs an electrical signal corresponding to the change of the induced strain in the film transducer caused by the dynamic force and analyzing the electrical signal to indicate the quality of the fruit. Apparatus for carrying out the method is also described and claimed.

4 Claims, 10 Drawing Sheets

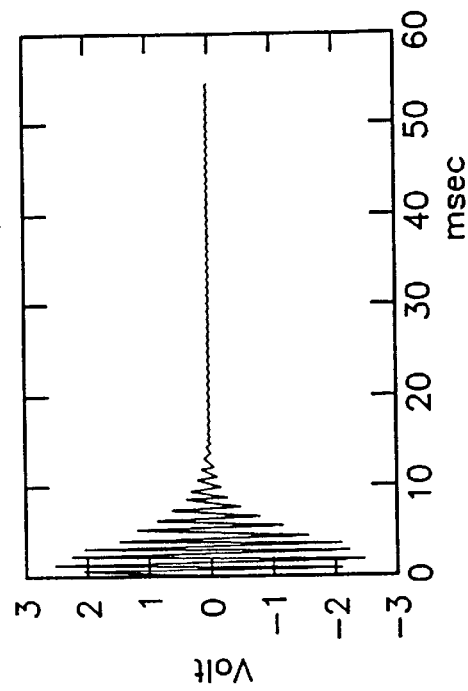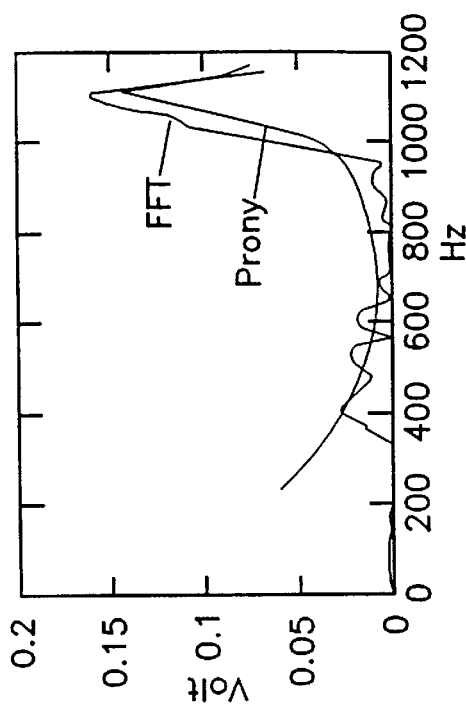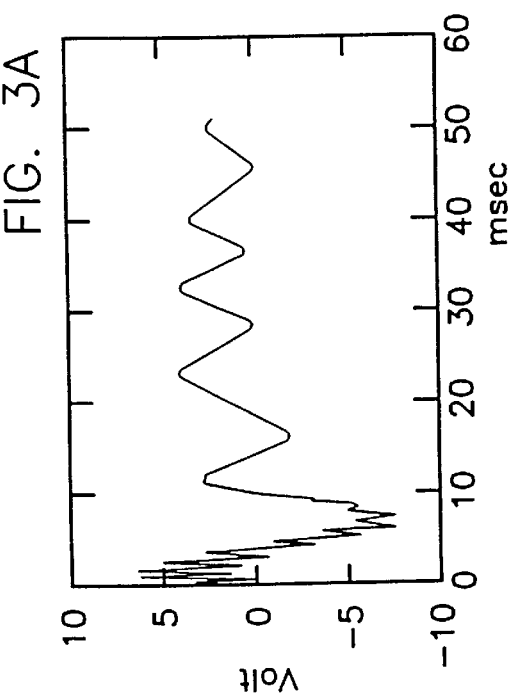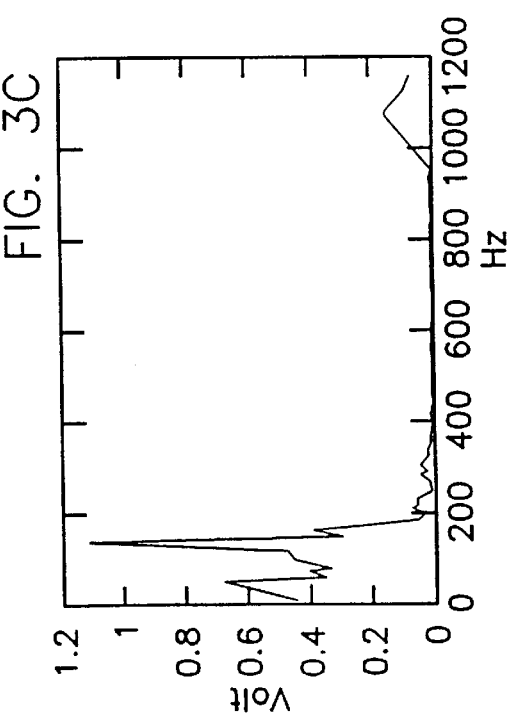

METHOD AND APPARATUS FOR TESTING THE QUALITY OF FRUIT

FIELD OF THE INVENTION

The present invention relates to methods and apparatus for testing the quality of fruit.

BACKGROUND OF THE INVENTION

High-value fresh agricultural products, particularly those intended for export, must be carefully handled and sorted in order to meet high quality standards. Many methods are available for detecting quality and for sorting according to external fruit properties, such as size, shape, color and external appearance. Internal properties, such as ripeness, taste, flavour, and internal damage, are generally determined indirectly, by linking the property to one or more external fruit properties, or are measured directly through destructive tests.

SUMMARY OF THE INVENTION

An object of the present invention is to provide a novel non-destructive method and apparatus for testing the quality of a fruit.

According to the present invention, there is provided a method of testing the quality of a fruit, comprising: applying a dynamic force to the fruit; detecting the mechanical response of the fruit to said dynamic force via a piezoelectric film transducer supported on a displaceable supporting member such that the film transducer is bent, to induce a strain therein, by said dynamic force and outputs an electrical signal corresponding to the rate of change of the induced strain in the film transducer caused by said dynamic force; and analyzing said electrical signal to indicate the quality of the fruit.

A piezoelectric film transducer is a relatively new type of transducer which has begun to find extensive use in acoustical applications, both in acoustical emitters and in acoustical receivers. One construction now commercially available includes a piezoelectric polymeric film of polyvinylidene fluoride having an electrically-conductive film coated on its opposite sides. The present invention utilizes such piezoelectric film transducers by supporting them on a displaceable supporting member so that the film transducer is bent by the dynamic force (as distinguished from a static force) to induce a strain in the film transducer. Since the induced strain varies with the rate of change of the applied dynamic force, the output of the film transducer will be a measurement of the rate of change of the applied dynamic force. It is this output which is analyzed to indicate the quality of the fruit.

According to further features of the invention as included in the preferred embodiments described below, the dynamic force applied to the fruit, to produce the mechanical response detected by the piezoelectric film transducer, may be an impact force applied mechanically, electromagnetically or pneumatically. The dynamic force may also be an impulse force or a vibrational force, such as applied mechanically by another piezoelectric film transducer, a conventional piezoelectric crystal transducer or a mechanical vibrator, or as applied acoustically by a loudspeaker, etc. The dynamic force may also be an inertial force applied by accelerating or decelerating the fruit.

According to further features included in many of the described preferred embodiments, the displaceable supporting member may be a resilient base, a flexible beam, or a pivotal arm.

According to still further features in the described preferred embodiments, the mechanical response of the fruit which is detected and analyzed may be the resonance frequencies of sonic waves produced in the fruit as a result of the dynamic force applied thereto, or may be the attenuation rate of sonic waves produced in the fruit as a result of the dynamic force applied thereto.

The invention also provides novel apparatus for testing the quality of a fruit in accordance with the above methods.

BRIEF DESCRIPTION OF THE DRAWINGS

The invention is herein described, somewhat diagrammatically and by way of example only, with reference to the accompanying drawings, wherein:

FIGS. 3A, 3B, 3C and 3D illustrate time and frequency responses of an apple tested in accordance with the invention;

DETAILED DESCRIPTION OF PREFERRED EMBODIMENTS

Figure 1:
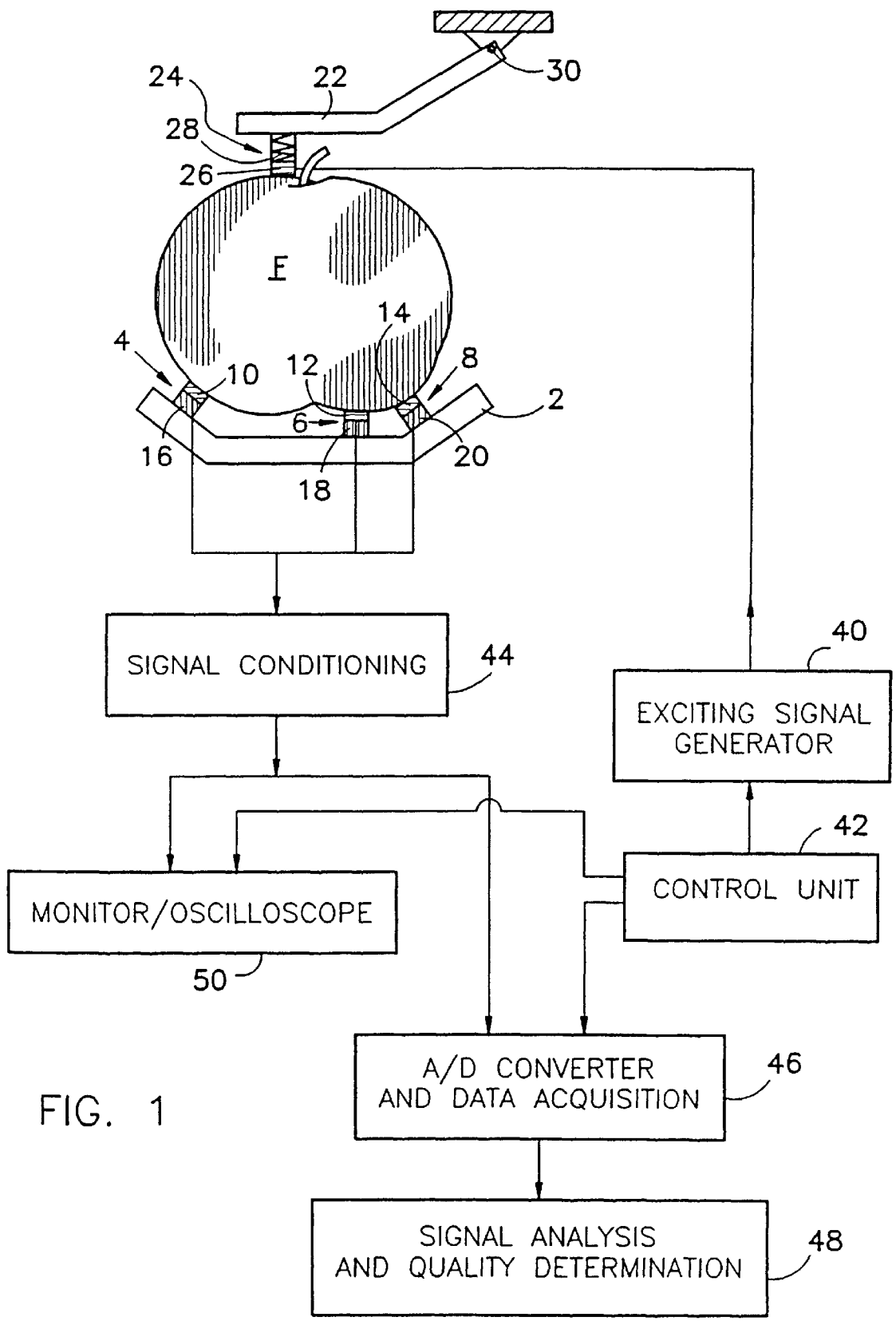
FIG. 1 illustrates one form of apparatus for testing the quality of a fruit in accordance with the present invention.

The apparatus illustrated in FIG. 1 comprises a fruit bed 2 for holding the fruit F, such as an apple, to be tested. The fruit bed 2 is equipped with one or more displaceable contact elements engaging the outer surface of the fruit F when received within the fruit bed. In the example illustrated, there are three such displaceable contact elements 4, 6, 8, thereby providing three points of contact with the outer lower surface of the fruit. Each contact element 4, 6, 8, includes a piezoelectric film transducer 10, 12, 14 in direct contact with the outer surface of the fruit F, and a resilient base or pad 16, 18, 20 pressing the piezoelectric film transducer into firm contact with the fruit.

The illustrated apparatus further includes an arm 22 pivotally mounted with respect to the fruit F within the fruit bed 2, and carrying a further displaceable contact element 24 for engagement with the outer upper surface of the fruit F. Displaceable contact element 24 includes a piezoelectric transducer 26, of the film type or of the crystal type, and a spring 28 serving as a resilient urging the transducer into firm contact with the outer surface of the fruit F. Arm 22 is pivotally mounted at 30 to bring contact element 24 into or out of engagement with the fruit F.

The piezoelectric transducer 26 engaging the upper surface of the fruit F serves as an exciter or transmitter for transmitting a dynamic force, e.g., a mechanical impulse force or a sonic vibrational force, to the fruit F; whereas the piezeoelectric film transducers 10, 12, 14 engaging the lower surface of the fruit serve as receivers for detecting the mechanical response of the fruit F to the applied dynamic force. Since the exciter transducer 26 applies a dynamic force, it may be of the piezoelectric film type or of the conventional crystal type. The detector transducers 10, 12, 14 are of the piezoelectic film type, and since they are supported on their respective resilient bases, the dynamic forces propagated through the fruit cause them to bend to induce strains in their respective film transducers, corresponding to the applied dynamic force. The piezoelectric film transducers 10, 12, 14 output electrical signals corresponding to the rate of change of the strains induced in them. These electrical signals are analyzed to indicate the quality of the fruit F under test.

Thus, the system illustrated in FIG. 1 includes an exciting signal generator 40 under the control of a control unit 42 for exciting the top transmitter piezoelectric transducer 26, to generate the dynamic force, e.g., a mechanical impulse force or sonic vibrational force, applied to the fruit F. The electrical signals generated by the receiver piezoelectric film transducers 10, 12, 14 are fed to a signal conditioning circuit 44 before being applied to an analog-to-digital converter 46. The latter circuit converts the analog output of the receiver transducers 10, 12, 14 to digital form, for analysis in the signal analysis and quality determination circuit or module 48. The output of the signal conditioning circuit 44 is also applied to a monitor/oscilloscope 50 for direct viewing.

It will be appreciated that only one piezoelectric film transducer, e.g., transducer 10 in FIG. 1, is needed to detect the mechanical response of the fruit to the dynamic force applied to it. It will also be appreciated that more than one transducer may be used as a transmitter, e.g., transducer 14 at the bottom of the fruit. It will be further appreciated that the measuring and control circuitry illustrated in FIG. 1 could be partly or completely embodied in a microprocessor rather than in discrete circuitry.

The piezoelectric film transducers in 10, 12, 14 (and also 26 if a film transducer is used) are commercially available polyvinylidene fluoride piezoelectric film coated on opposite sides with a conductive coating, such as of silver.

Figure 2:
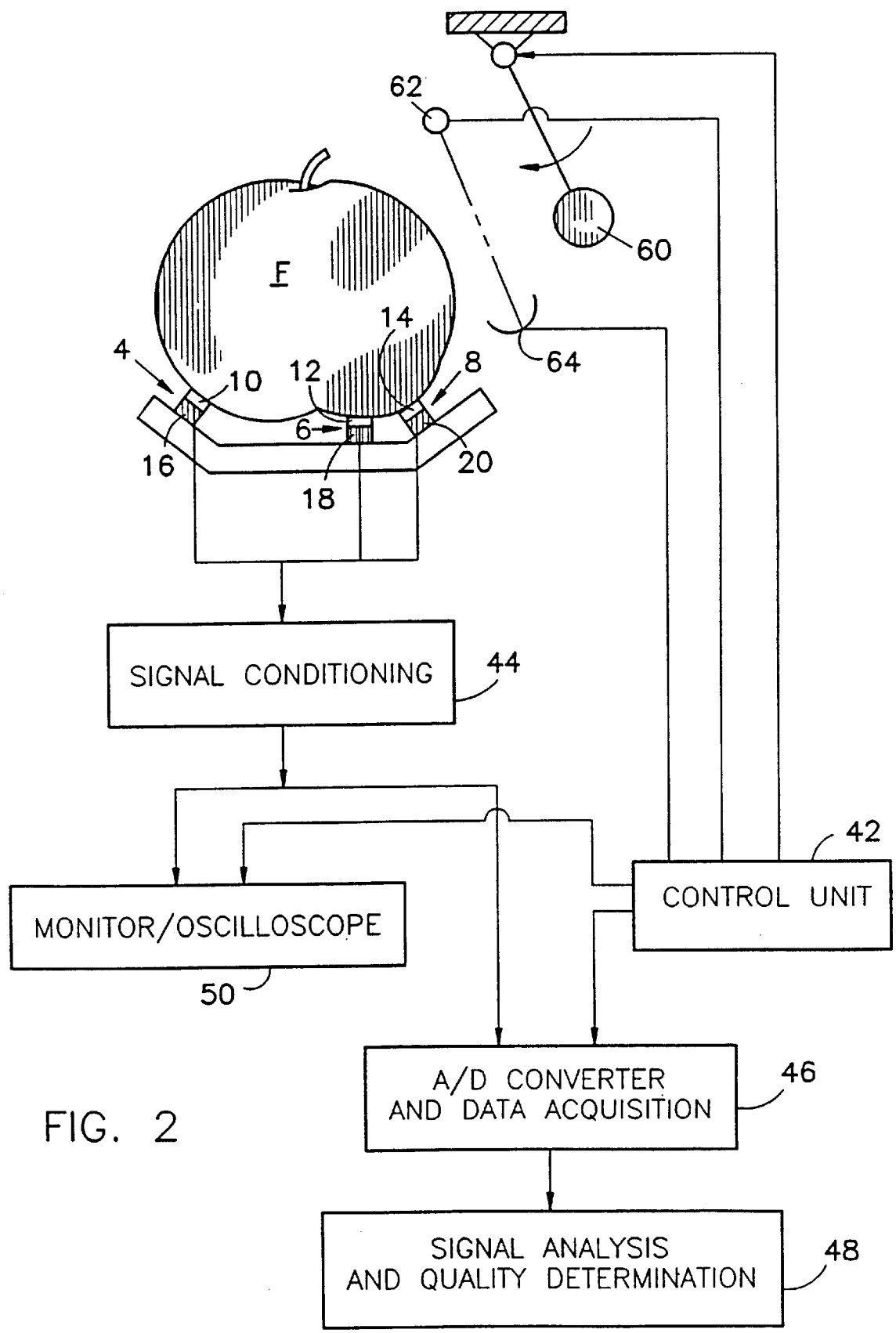
FIG. 2 illustrates a second form of apparatus for testing the quality of a fruit in accordance with the present invention.

FIG. 2 illustrates apparatus similar to that of FIG. 1, and to facilitate understanding, the corresponding parts are identified by the same reference numbers. In the apparatus of FIG. 2, however, the fruit F under test is subjected to an impact force. For this purpose, the transmitter piezoelectric transducer 26 is omitted and is replaced by an impact element in the form of a pendulum 60 which applies a predetermined impact force against the fruit F under test. The system illustrated in FIG. 2 further includes a light source 62 and a photodiode 64 for detecting the instant just before the fruit F is impacted by the pendulum 60.

In the apparatus illustrated in FIG. 2, the impact element 60 is mechanically applied by a small wooden rod pendulum. The instant of impact, or just before impact, by the pendulum 60 is detected by photodiode 64 connected to the control unit 42. The signal so produced by the photodiode 64 is used to trigger the dynamic sensor system including the piezoelectric film transducers 10, 12, 14. While FIG. 2 illustrates the instant just before impact, the point of impact being detected by the photodiode 64, it will be appreciated that this could also be detected by the change in the output of one or all of the piezoelectric film transducers 10, 12, 14.

Various varieties of fruit were tested by the apparatus illustrated in FIG. 2. FIG. 3 illustrates an example of the recorded response of an apple in time domain before and after high-pass filtering of 300 Hz (FIGS. 3a and 3b) and their Fast Fourier Transforms (FFTs, FIGS. 3c and 3d, repectively). These figures show that the high resonance frequencies of fruit response may be super-imposed on a basic, low frequency signal that may be caused by the fruit bed 2. The higher frequencies represent the real natural frequencies of the tested fruit.

The low resonance frequency of the tested fruit and the spring constant of the fruit also relate to the mass of the body, and therefore measuring the low resonance frequency of the fruit may also be used for determining the weight of the fruit according to known techniques.

Figure 4:
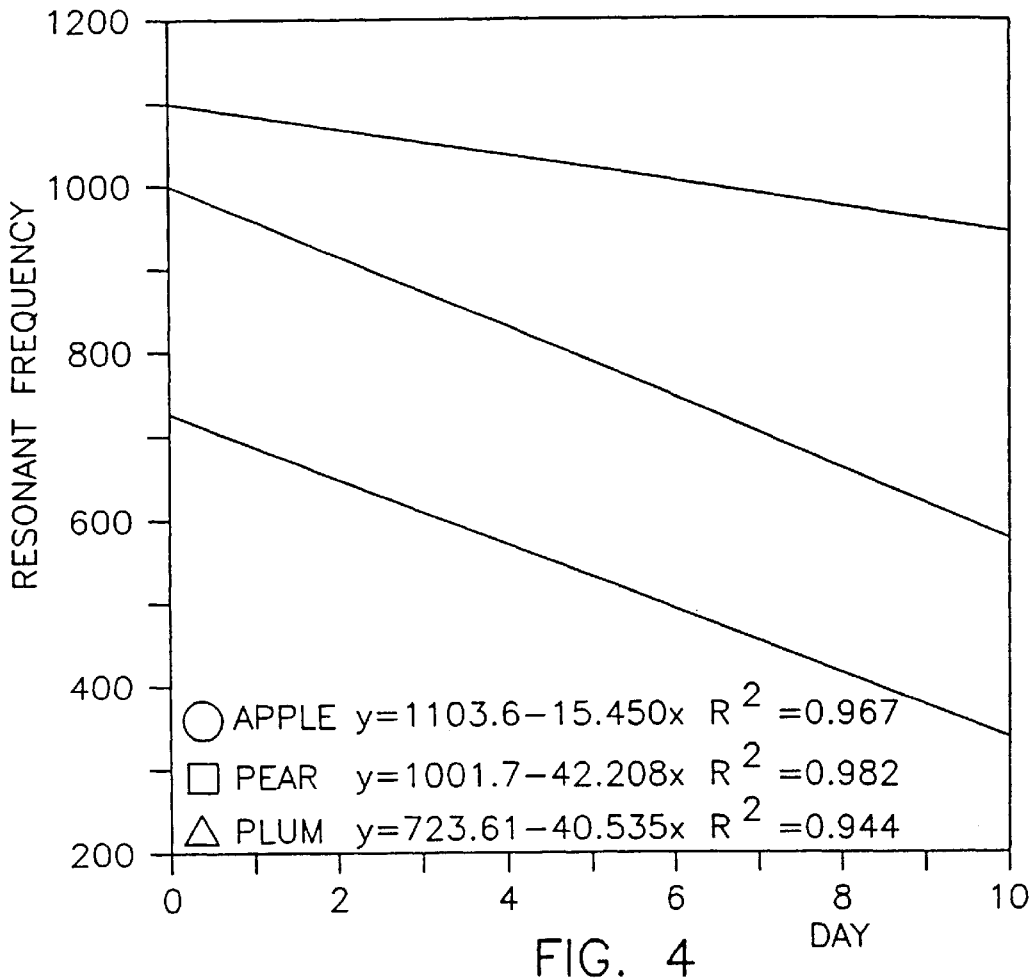
FIG. 4 illustrates the frequency response of several fruit varieties tested in accordance with the present invention.

FIG. 4 illustrates the decline of the first resonance frequencies of various fruits during eight days. These tests showed a decrease of 1.4% to 5.5% per day in the resonance frequency of the various fruits, thereby showing that the resonance frequency provides an indication of the freshness of the fruit.

FIGS. 5–14 illustrate other arrangements in which the fruit may be excited, and its mechanical response may be detected, to provide an indication of the quality of the fruit.

Figure 5:
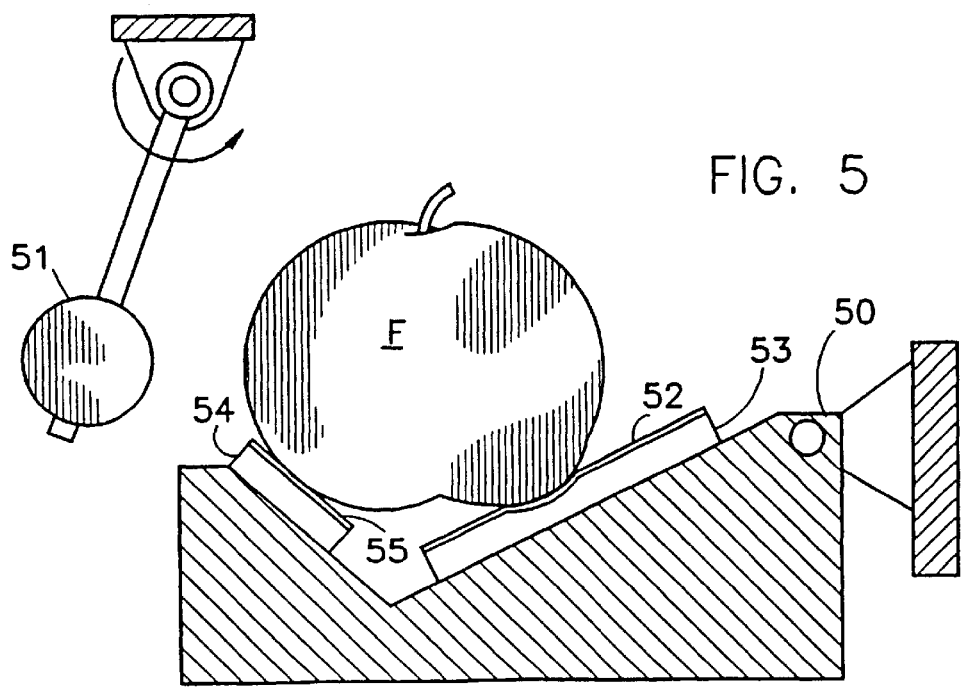
FIGS. 5, 6, 6A, 7, 8, 9, 10, 11, 12, 12A, 13 and 14 illustrate further forms of apparatus for testing the quality of a fruit in accordance with the present invention, FIGS. 6a and 12a being top plan views of FIGS. 6 and 12, respectively.

Thus, FIG. 5 illustrates an arrangement wherein the fruit F is received in a bed 50 and is impacted by a pendulum 51, while its mechanical response is detected by a piezoelectric film transducer 52 supported on a resilient base 53 on which the fruit F rests. A side wall of bed 50 is provided with a resilient damping element 54 which may also include a piezoelectric film transducer 55 on its outer surface in contact with the fruit F. The resilient bases 53 and 54 may be soft rubber pads or the like. The arrangement illustrated in FIG. 5 may also include a light source and a photodiode (not shown) to detect the instant before impact of the pendulum 51 with the fruit F, or may detect the instant of impact by the output of the transducer 55.

Figure 6:
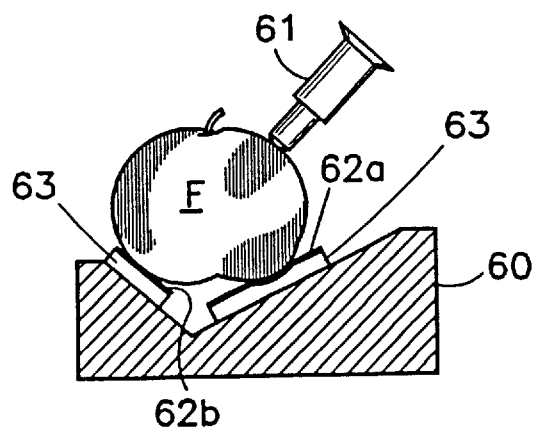
Figure 6A:
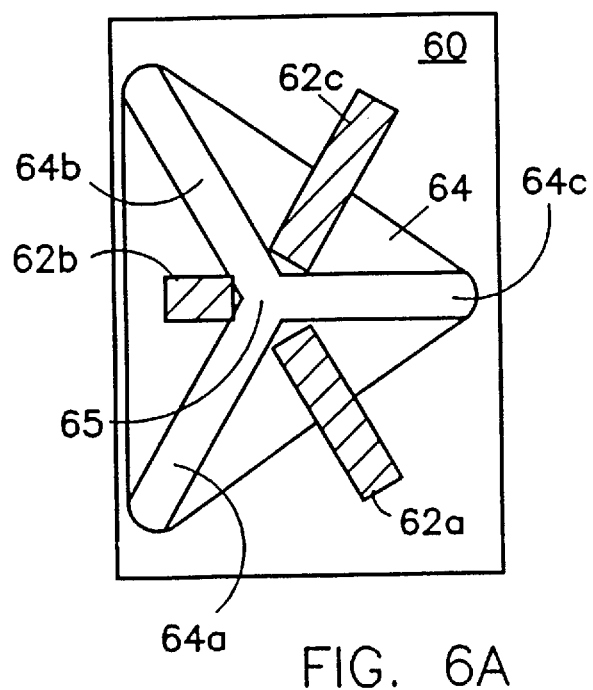

FIGS. 6 and 6a illustrate another arrangement including a bed 60 for receiving the fruit F, in which the dynamic force applied to the fruit is effected by a pneumatically-actuated impact element 61. The response to the impact is detected by three piezoelectric film transducers 62a, 62b, 62c, each supported on a resilient base or pad 63. The bed 60 is formed with a triangular cavity 64, whose floor is formed with recesses 64a, 64b, 64c extending between a common intersection point 65 and the three corners of the cavity. The three piezoelectric film transducers 62a–62c extend from the common intersection point 65 to one of the sides of the triangle. In such an arrangement the fruit F being tested is contacted only at three points by the piezoelectric film transducers.

Figure 7:
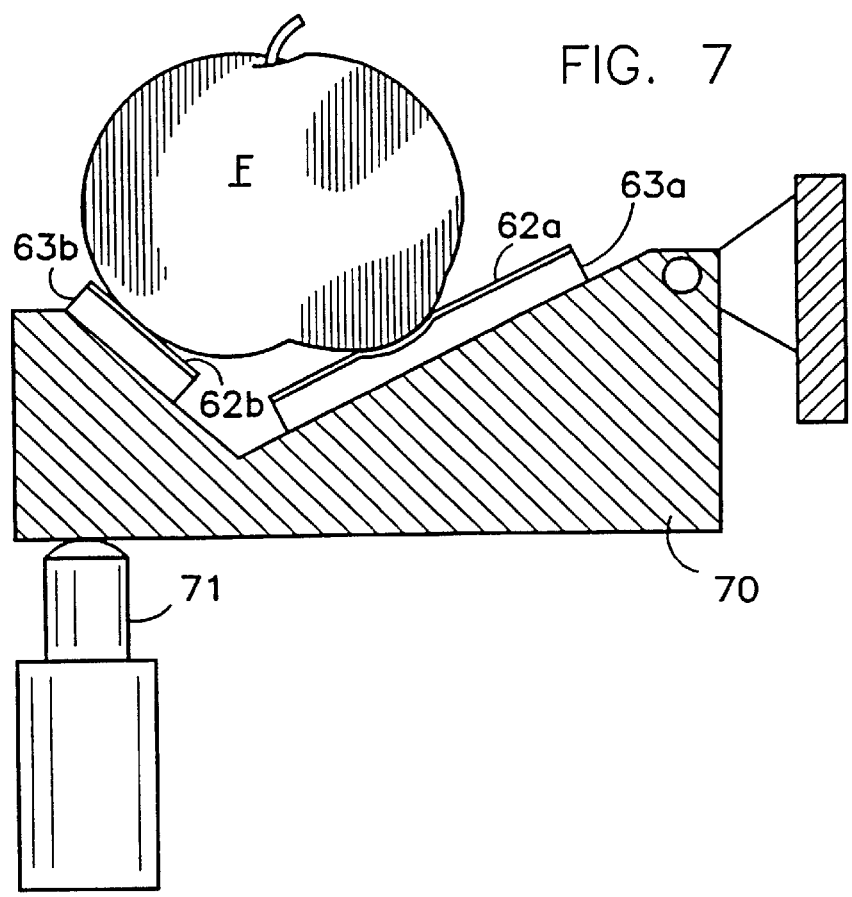

FIG. 7 illustrates another arrangement wherein the fruit bed 70 receiving the fruit F being tested is impacted by an electromechanically-actuated impact element 71; and the mechanical response to the impact is detected by a plurality of piezoelectric film transducers 62a, 62b, each supported on a resilient base 63a, 63b. Although FIG. 7 illustrates two such detectors, there would preferably be three such detectors arrayed as shown in FIG. 6. The same applies with the other arrangements described below.

Figure 8:
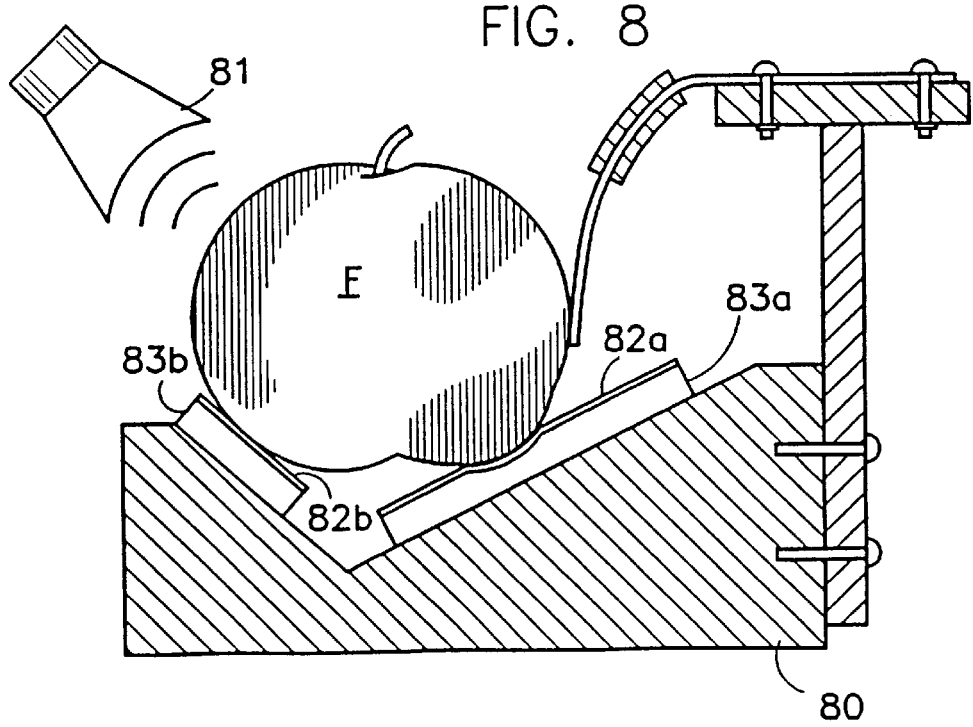

FIG. 8 illustrates an arrangement including a fruit bed 80 receiving the fruit F to be tested, wherein the dynamic force applied to the fruit is a vibrational acoustical force applied by a loudspeaker 81. The mechanical response of the fruit to the applied force is detected by piezoelectric film transducers 82a, 82b each supported on a resilient base 83a, 83b, which may be arranged as described above with respect to FIGS. 6 and 7. In addition, the arrangement illustrated in FIG. 8 includes a further pair of piezoelectric film transducers 64a, 64b, mounted on the opposite sides (or on only one side) of an elastic beam 65, such as a leaf spring, biassed against the side of the fruit F being tested.

Figure 9:
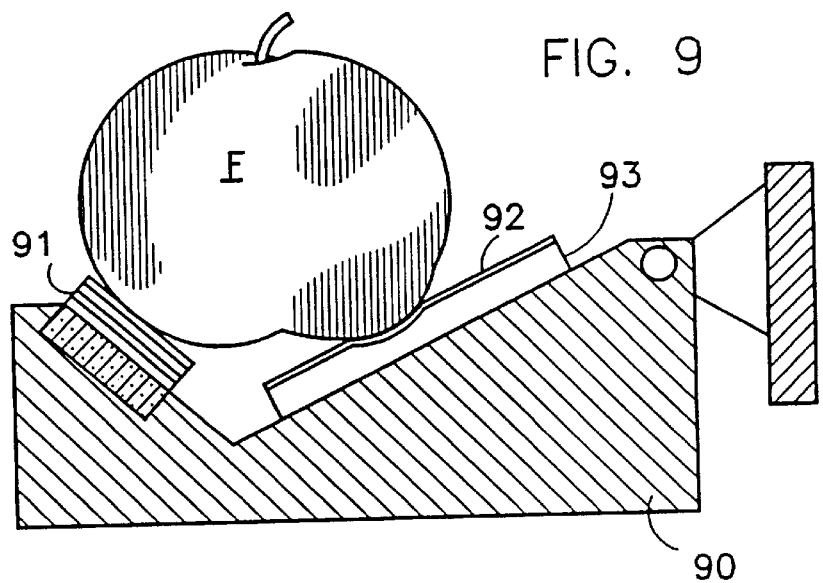

FIG. 9 illustrates a further arrangement including a fruit bed 90 in which the fruit F to be tested is excited by a piezoelectric crystal transducer 91, and the mechanical response of the fruit is detected by a piezoelectric film transducer 92 supported on a resilient base 93.

Figure 10:
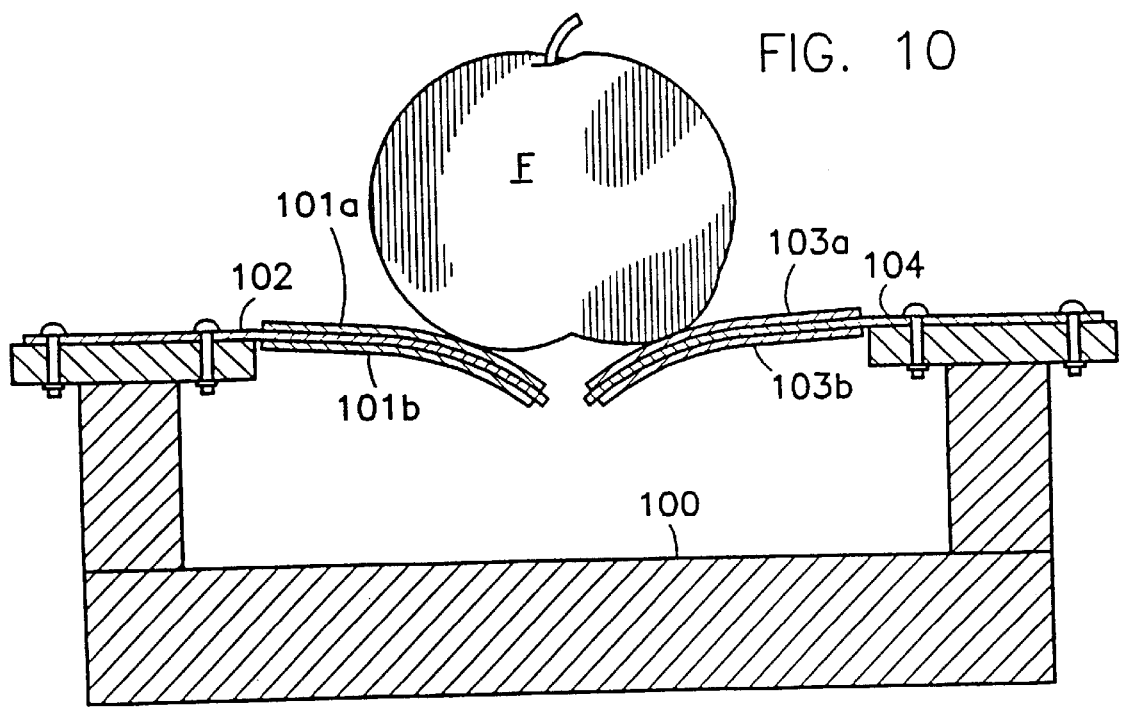

FIG. 10 illustrates an arrangement including a bed 100 in which the fruit F to be tested is excited by a pair of piezoelectric film transducers 101a, 101b, mounted on opposite sides of an elastic beam in the form of a leaf spring 102; and the mechanical response of the fruit to the excitation is detected by another pair of piezoelectric film transducers 103a, 103b, mounted on the opposite sides (or on only one side) of another elastic beam 104.

Figure 11:
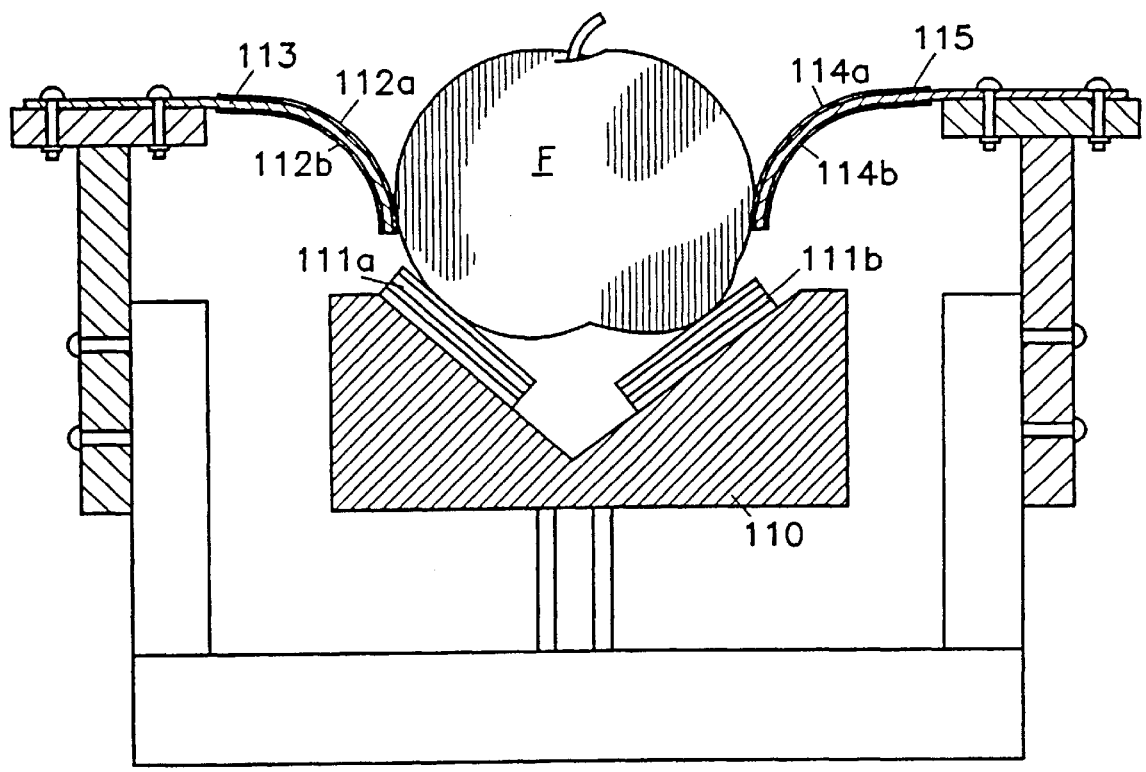

FIG. 11 illustrates a further arrangement including a bed 110 in which the fruit F to be tested is excited by a pair of piezoelectric elements 111a, 111b (e.g., crystals or films) supporting the fruit, and in which the mechanical response of the fruit to the excitation is detected by a first pair of piezoelectric film transducers 112a, 112b, mounted on opposite sides (or on only one side) of an elastic beam, e.g., a leaf spring, 113 and urged thereby into contact with one side of the fruit F, and a second pair of piezoelectric film tranducers 114a, 114b, mounted on opposite sides (or on only one side) of an elastic beam 115 and urged against the opposite side of the fruit.

Figure 12:
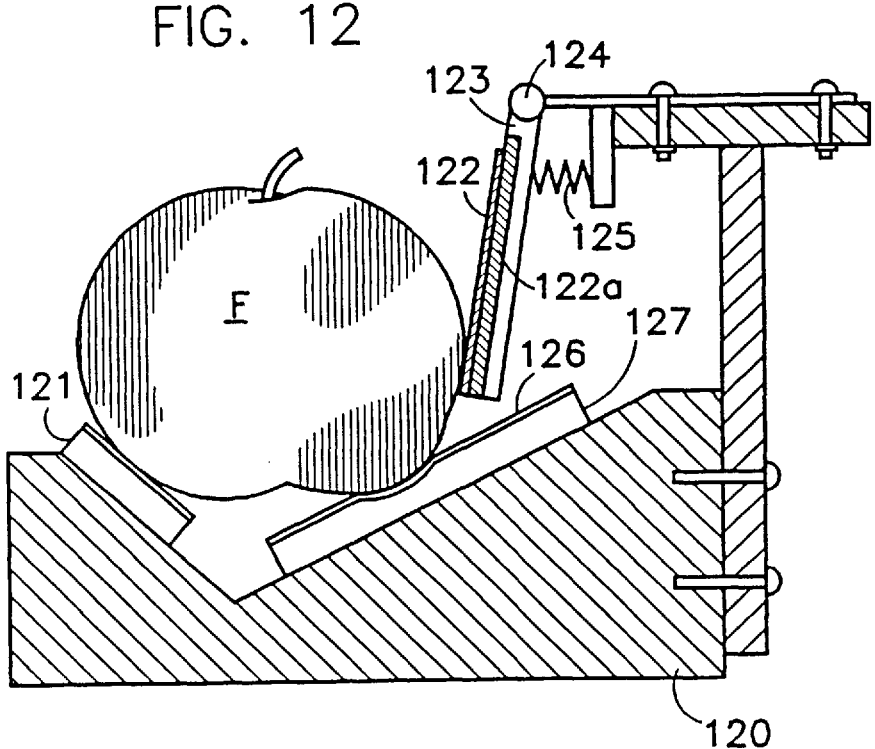
Figure 12A:
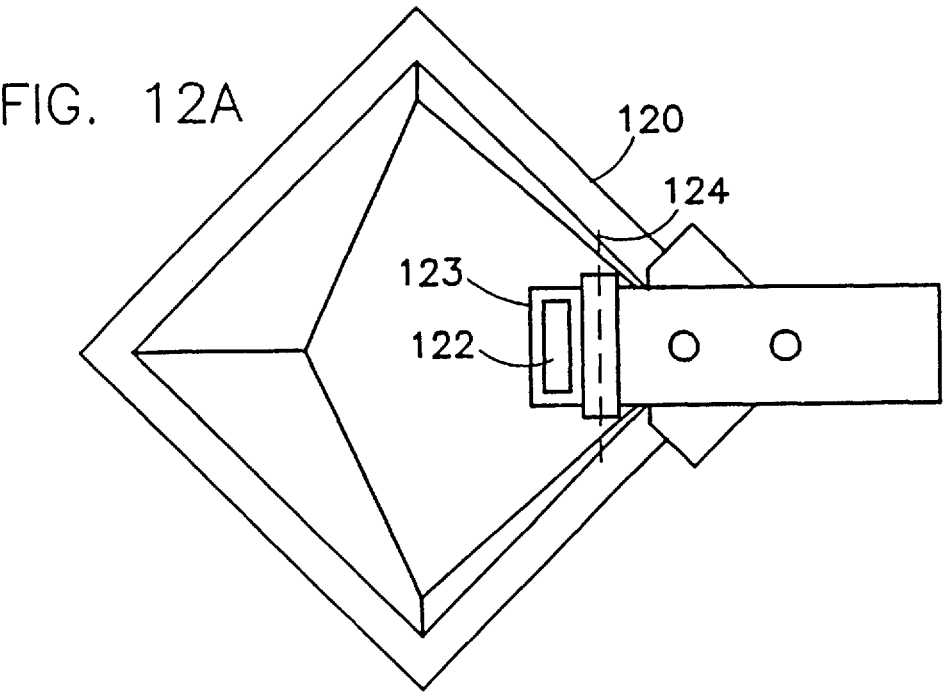

FIGS. 12 and 12a illustrate a further arrangement including a bed 120, in which the fruit F being tested is excited by a piezoelectric crystal transducer 121, and the mechanical response thereto is detected by a piezoelectric film transducer 122 supported on the outer face of a resilient pad 122a carried on one side of an arm 123 pivoted at 124 and urged into contact with the fruit F by a spring 125. The opposite side of bed 120 may carry a second piezoelectric film transducer 126 supported on a resilient pad 127.

Figure 13:
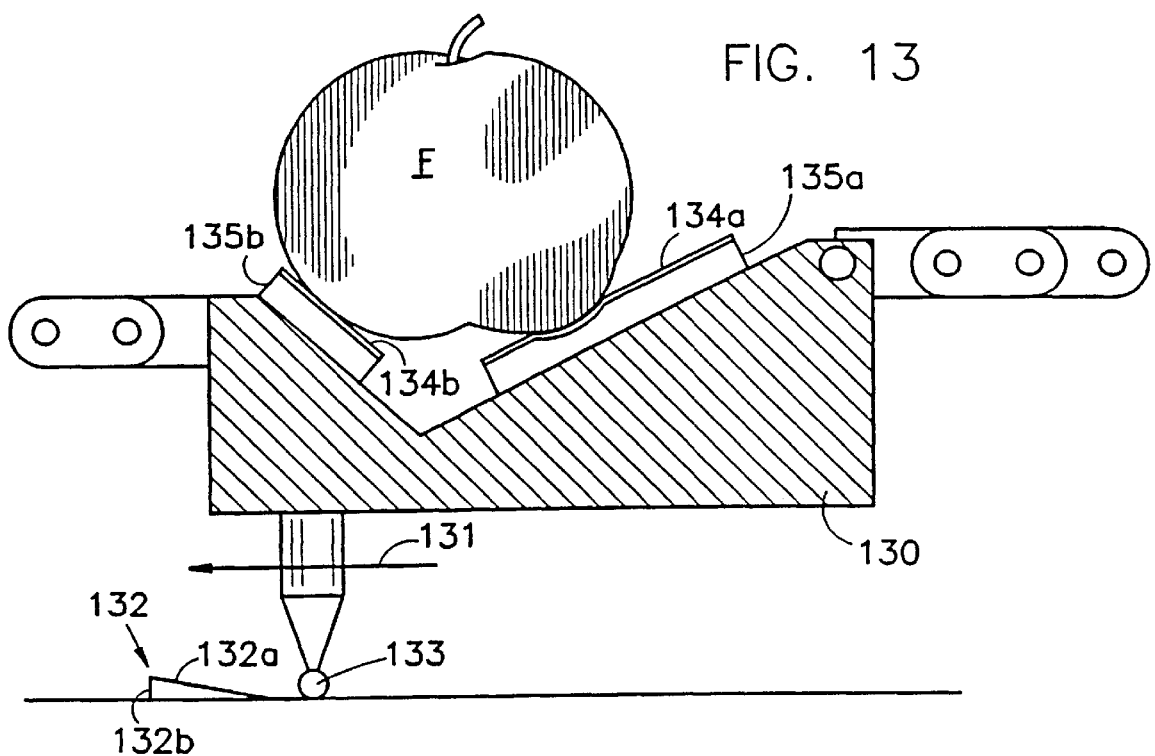

FIG. 13 illustrates a further arrangement including a bed 130 in which the dynamic force applied to the fruit F for exciting it is an inertial force produced by the sudden acceleration and/or deceleration of the fruit. In the illustrated arrangement, the bed is driven in the direction of the arrow 131 and engages a cam 132 having an upwardly inclined face 132a and vertical face 132b engaged by a cam follower 133, which decelerates the bed in the upward direction, followed by a sharp drop which more quickly accelerates the bed and fruit in the opposite direction, to apply inertial forces to the fruit F. The response of the fruit to the inertial forces so applied is detected by a pair of piezoelectric film transducers 134a, 134b, each mounted on a resilient pad 135a, 135b.

Figure 14:
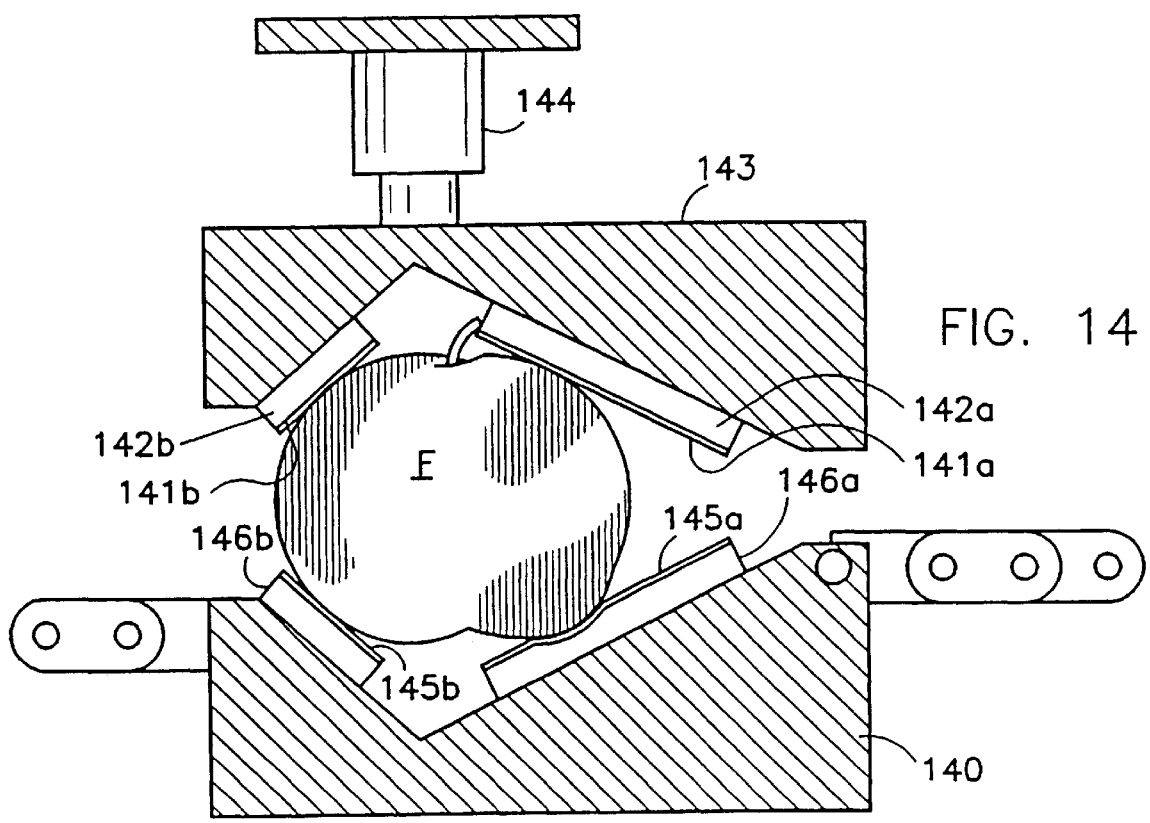

FIG. 14 illustrates an arrangement including a fruit bed 140 in which the excitation of the fruit F is effected by a pair of piezoelectric force transducers 141a, 141b, each mounted on a resilient pad 142a, 142b. Both are carried by a head 143 movable by a cylinder 144 towards and away from the fruit bed 140. Head 143 may also be moved in the same direction as the fruit bed, if the fruit bed is a travelling one. The response to the force so applied to the fruit F is detected by a pair of piezoelectric film transducers 145a, 145b each supported on a resilient pad 146a, 146b.

While the invention has been described with respect to several preferred embodiments, it will be appreciated that many variations may be made. For example, in the arrangement illustrated in FIG. 14, all the transducers could be mounted on the head 143. Many other variations, modifications and applications of the invention will be apparent.

We claim:

1. A method of testing the quality of a fruit, comprising:

applying a dynamic impact force to the fruit;

detecting the mechanical response of the fruit to said dynamic force via a piezoelectric film transducer directly mounted onto, and flush with, a top surface of a displaceable resilient pad, which is in turn mounted on a rigid base such that the film transducer is bent by said dynamic impact force, to induce a strain in said film transducer, and said film transducer outputs an electrical signal corresponding to the change of the induced strain in the film transducer caused by said dynamic force; and analyzing said electrical signal to indicate the quality of the fruit.

2. The method according to claim 1, wherein said mechanical response is the resonance frequencies of sonic waves produced in the fruit as a result of the dynamic force applied thereto.

3. Apparatus for testing the quality of a fruit, comprising:

a holder for receiving the fruit to be tested;

a dynamic force impactor for applying a dynamic force to the fruit in said holder;

a piezoelectric film transducer directly mounted onto, and flush with, a top surface of a displaceable resilient pad, which is in turn mounted on a rigid base such that the film transducer is bent, to induce a strain in said film transducer, by said dynamic force and said film transducer outputs an electrical signal corresponding to the change of the induced strain in the film transducer caused by said dynamic impact force; and an analyzer for analyzing said electrical signal outputted by the piezoelectric film transducer to indicate the quality of the fruit.

4. The apparatus according to claim 3, wherein said analyzer analyzes the resonance frequencies of sonic waves produced in the fruit as a result of the dynamic force applied thereto.

* * * * *